United States Patent [19]

Shibata et al.

[11] Patent Number: 5,735,274
[45] Date of Patent: Apr. 7, 1998

[54] APPARATUS AND METHOD FOR ANALYZING PARTICLES INCLUDING SHIFTING A JUDGEMENT REGION

[75] Inventors: Kimiyo Shibata, Kakogawa; Yoshihiro Mishima, Kobe, both of Japan

[73] Assignee: Toa Medical Electronics Co. Ltd., Hyogo, Japan

[21] Appl. No.: 675,260

[22] Filed: Jul. 3, 1996

[30] Foreign Application Priority Data

Jul. 4, 1995 [JP] Japan ................... 7-168750

[51] Int. Cl.$^6$ ................... A61B 5/000
[52] U.S. Cl. ................... 128/637; 364/555
[58] Field of Search ................... 73/865.5; 128/633, 128/637, 664, 665; 356/39, 335, 336, 338; 364/413.08, 413.1, 555

[56] References Cited

U.S. PATENT DOCUMENTS

| | | | |
|---|---|---|---|
| 5,006,986 | 4/1991 | Inoue | 364/413.08 |
| 5,040,112 | 8/1991 | Marshall et al. | 364/413.08 |
| 5,408,307 | 4/1995 | Yamamoto et al. | 356/39 |
| 5,469,375 | 11/1995 | Kosaka | 364/413.08 |
| 5,532,943 | 7/1996 | Asano et al. | 364/555 |
| 5,555,198 | 9/1996 | Asano | 364/413.08 |

*Primary Examiner*—Jennifer Bahr
*Assistant Examiner*—Bryan K. Yarnell

[57] ABSTRACT

An apparatus and method for analyzing particles includes a distribution data preparation device for measuring parameters that characterize particles contained in a specimen and for preparing a distribution data of the particles in a coordinate space based on the parameters, a judgement region storage device for storing in advance a predetermined judgement region in the coordinate space, a base point extraction device for extracting, when the distribution data forms at least one group, a group base point that shows a position of the group, a judgement region correction device for correcting a position of the judgement region in the coordinate space by referring to each group base point extracted every time a distribution data is prepared by the distribution data preparation device, and a judgement device for judging the specimen based on the particles present within the corrected judgement region.

20 Claims, 17 Drawing Sheets

5,735,274

APPARATUS AND METHOD FOR ANALYZING PARTICLES INCLUDING SHIFTING A JUDGEMENT REGION

BACKGROUND OF THE INVENTION

1. Field of the Invention

The present invention relates to an apparatus for analyzing particles and, more particularly, to an apparatus for making a scattergram with parameters characterizing the particles in a specimen and for judging the specimen based on the scattergram.

2. Description of the Related Arts

Conventionally, such an apparatus for analyzing particles employs measuring the parameters that characterize the particles contained in a specimen, preparing a scattergram by plotting the parameters, setting a judgement region in a scattergram in advance, and examining the particles appearing in the region so as to analyze the specimen.

However, when the same specimen is analyzed in a plurality of apparatuses for analyzing particles, the position of the particles plotted in a scattergram might possibly be slightly different due to the minute difference in measurement properties between the apparatuses. Also, when two different specimens are analyzed in the same apparatus for analyzing particles, the group of particles that ought to be plotted at approximately the same place in a scattergram might possibly be plotted at somewhat different places due to the difference between the specimens. Therefore, if the judgement region is fixedly set in a scattergram, there is a possible danger of erroneously analyzing the specimens.

SUMMARY OF THE INVENTION

The present invention has been made in view of the above circumstances and provides an apparatus for analyzing particles which is capable of absorbing the differences between the apparatuses and between the specimens by suitably shifting the judgement region with respect to a group in a scattergram.

The present invention provides an apparatus for analyzing particles including a distribution data preparation section for measuring parameters that characterize particles contained in a specimen and for preparing distribution data of the particles in a coordinate space based on the parameters, a judgement region storage for storing in advance a predetermined judgement region in the coordinate space, base point extractor means for extracting, when the distribution data forms at least one group, a group base point that shows a position of the group, judgement region corrector for correcting a position of the judgement region in the coordinate space by referring to each group base point extracted every time distribution data is prepared by the distribution data preparation section, a judgement section for judging the specimen based on the particles present within the corrected judgement region.

DETAILED DESCRIPTION OF THE PREFERRED EMBODIMENTS

The particles to be analyzed with the apparatus for analyzing particles according to the present invention include cells in a body fluid, blood cells, minute particles that constitute inorganic powders, and the like.

In the present invention, to measure parameters that characterize particles is to electrically or optically measure parameters representing the size and the shape of the particles, i.e. the electric resistance, the forward or side scattered light intensity, and the fluorescence intensity.

To prepare distribution data of the particles in a coordinate space based on the parameters is, for example, to plot the frequency at coordinates representing each particle in a two-dimensional coordinate plane with x and y axes representing two different parameters so as to prepare a two-dimensional frequency distribution (scattergram).

To store in advance a predetermined judgement region in distribution data is, for example, if the specimen is a blood sample, to set in advance a specific region where abnormal particles such as blast cells, immature granulocytes, left shifts, and nucleated mature granulocytes are expected to appear.

The at least one group formed by a distribution data is, for example, if the specimen is a blood sample, a group of monocytes, lymphocytes, eosinophils, or granulocytes other than eosinophils (i.e., neutrophils, basophils) classified on the distribution data.

As the group base point representing the position of the group, it is possible to use, for example, the center of gravity of the group (mechanical center of gravity when a unit mass is given to each of the particles appearing in the distribution data) which provides a stable (invariable) position relative to the judgement region. However, when a plurality of stable groups are present in the distribution data, the group base point may be a point determined as a center of gravity of at least two groups included therein.

The correction by the correction section of the position of the judgement region by referring to the group base point represents, for example, the following operation. The storage for storing judgement regions stores in advance a region base point representing the position of the judgement region The correction section corrects the position of the judgement region so that the relative position of the group base point and the region base point is maintained under a specific relation, namely, to be constant.

The distribution data preparation section, the judgement region storage section, the base point extraction section, the judgement region correction section, and the judgement section may be integrally formed with a microcomputer or a personal computer.

EXAMPLE

Figure 1:
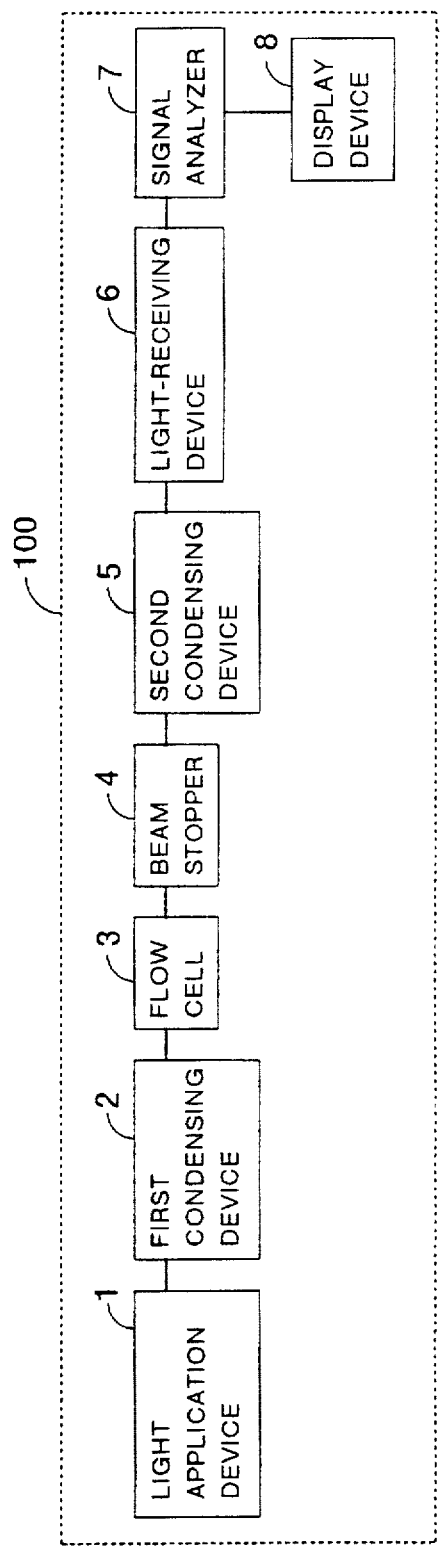
FIG. 1 is a block diagram showing a preferred example of the present invention.

FIG. 1 shows a fundamental construction of the apparatus for analyzing particles illustrating an embodiment of the present invention. The apparatus 100 for analyzing particles includes a flow cell 3 for letting cells flow in a line, a light application device 1 for applying a laser light onto cells flowing in the flow cell 3, a light-receiving device 6 having a light-receiving sensor partitioned into at least two sections capable of detecting each of the two kinds of forward scattered light scattered by the cell, a first condensing device 2 for condensing the laser light emitted from the light application device 1 into the flow cell 3, a second condensing device 5 for condensing the two kinds of forward scattered light scattered by the cell so that the two kinds of forward scattered light are approximately parallel to the optical axis of the laser light emitted from the light application device 1, and a beam stopper 4 for stopping the passage of direct light from the light application device 1.

Also, the apparatus 100 for analyzing particles includes a signal analyzer 7 for analyzing a pulse signal of each of the two kinds of forward scattered light detected by the light-receiving device 6. The apparatus 100 for analyzing particles lets the leukocytes to flow through the flow cell 3, detects the two kinds of forward scattered light with the light-receiving device 6, the two kinds of forward scattered light being scattered by the leukocytes flowing in a narrowed stream through the flow cell 3, analyzes the leukocytes with the signal analyzer 7, and displays the result of analysis with a display device 8.

Figure 2:
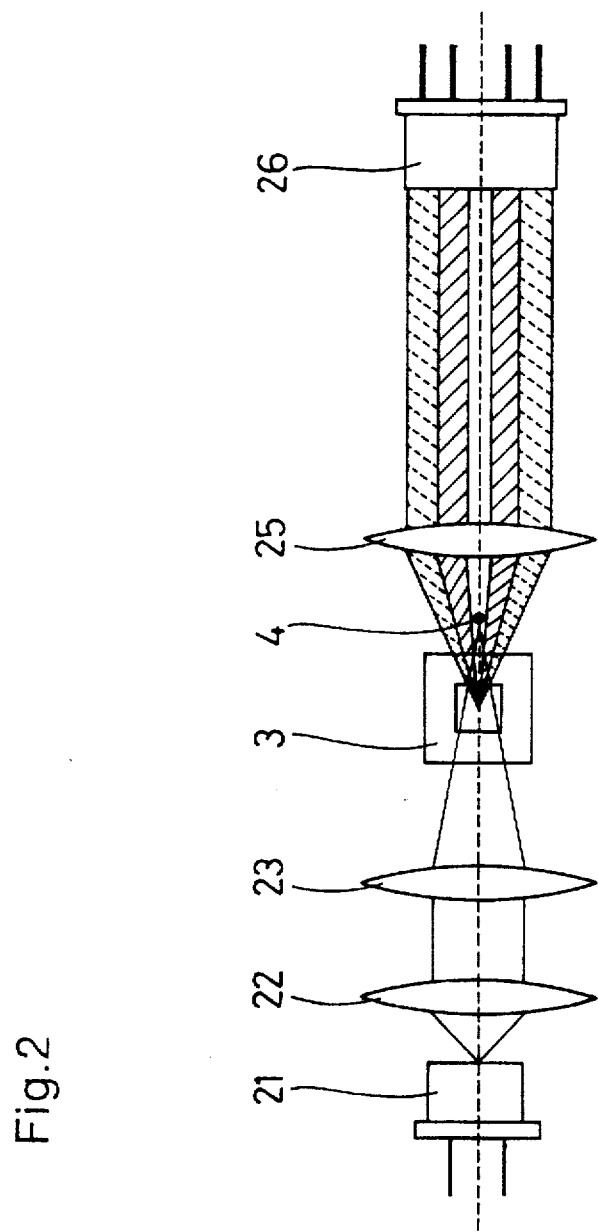
FIG. 2 is a detailed view showing an essential part of FIG. 1.

FIG. 2 is a detailed view of an essential part of FIG. 1. Referring to FIG. 2, the reference numeral 21 represents a semiconductor laser serving as the light application device 1, which may be, for example, a semiconductor laser TOLD9421 manufactured by Toshiba (with light output power 5 mW at the maximum and output wavelength 650 nm).

A collimator lens 22, and a condenser lens constitute the first condensing device 2. The laser light emitted from the semiconductor laser 2 is condensed to a portion in the flow cell 3 where particles flow. In the flow cell 3, a blood sample processed with a reagent is narrowed into a fine stream (with a sheath flow formed), and is let to flow in a direction from the back side to the front side of the sheet of FIG. 2.

A beam stopper 4 and a collector lens 25 serving as the second condensing device 5 are disposed on the side opposite to the side where the semiconductor laser 21 is located, namely, in the rear of the flow cell 3. At some distance therefrom is disposed one photodiode 26 serving as the light-receiving device 6. The beam stopper 4 is an oblong board which extends in a direction of the stream in the flow cell for stopping the laser light (direct light) in the central portion transmitted through the flow cell 8.

The collector lens 25 is a lens for condensing the forward scattered light scattered by a cell flowing in the flow cell 3 so that the forward scattered light will be parallel to the optical axis. The collector lens 25 constitutes the second condensing device 5.

The photodiode 26 receives the forward scattered light which has been made parallel to the optical axis by the collector lens 25. Here, the photodiode has partitioned light-receiving surfaces that can receive two kinds of forward scattered light among the scattered lights.

Figure 3:
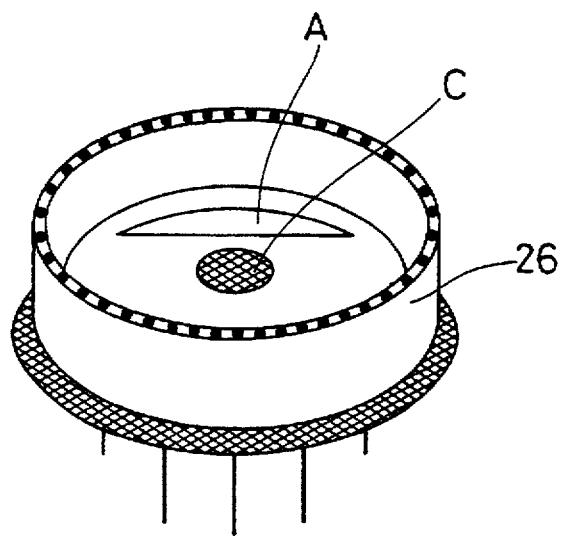
FIG. 3 is a detailed perspective view showing an essential part of FIG. 2.
Figure 4:
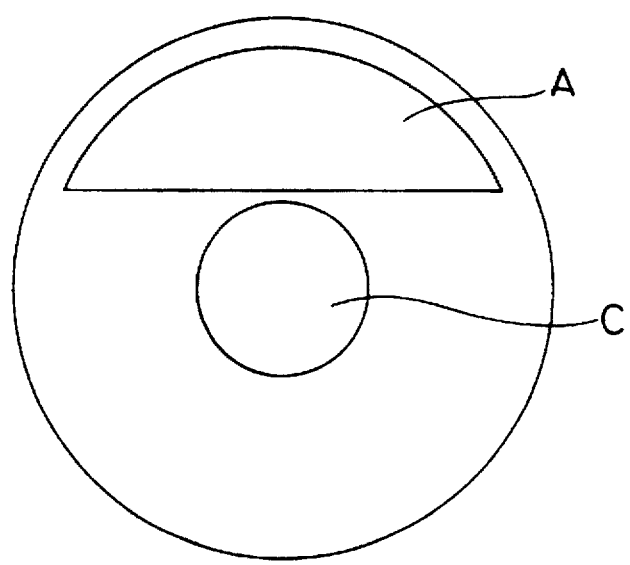
FIG. 4 is an explanatory view showing an essential part of FIG. 2.

FIG. 3 is a perspective view of the photodiode FIG. 4 is an explanatory view showing the shape of the light-receiving surface.

The photodiode 26 comprises a circular light-receiving surface C in the central portion, and a semi-circular light-receiving surface A in the peripheral portion, as shown in FIG. 4.

The photodiode 26 detects a low-angle forward scattered light with an angle of 1° to 5° relative to the optical axis and a high-angle forward scattered light with an angle of 6° to 20° relative to the optical axis with the light-receiving surface C and the light-receiving surface A, respectively.

The low-angle forward scattered light reflects the size of the cell, whereas the high-angle forward scattered light reflects the inner morphology of the cell. Analysis of the signals obtained from these scattered lights makes it possible to count and classify the cells.

Here, the circular light-receiving surface C is formed to have, for example, a diameter of 1.5 mm, and the semicircular light-receiving surface A is formed, for example, as a part of a circle having a diameter of about 6 mm.

The photodiode 26 is housed in a metal can-type vessel shown in FIG. 3 in the same manner as a photodiode usually used, and comprises several terminals for outputting electric pulse signals corresponding to the intensities of the scattered lights received.

These terminals are connected to a signal analyzer 7 as shown in FIG. 1. The signal analyzer 7 is constructed with an amplifier circuit, a peak detector circuit, an A/D converter circuit, a microcomputer, and the like. The micro-computer comprises a CPU, a ROM, a RAM, and the like. An input device such as a key board or a mouse is connected to the microcomputer depending on the needs. The display 8 is constructed with a CRT, a LCD, a printer, or the like. The electric pulse signals output from the photodiode 26 are two kinds of signals corresponding to the light intensities of the low-angle forward scattered light and the high-angle forward scattered light, and are output for each cell passing through the region in the flow cell 3 irradiated with light.

On receiving the above electric pulse signals, the signal analyzer 7 measures the peak value, the pulse width, the area of the pulse waveform, and the like of the pulse to derive data necessary for cell analysis, thereby counting and classifying the cells.

Figure 5:
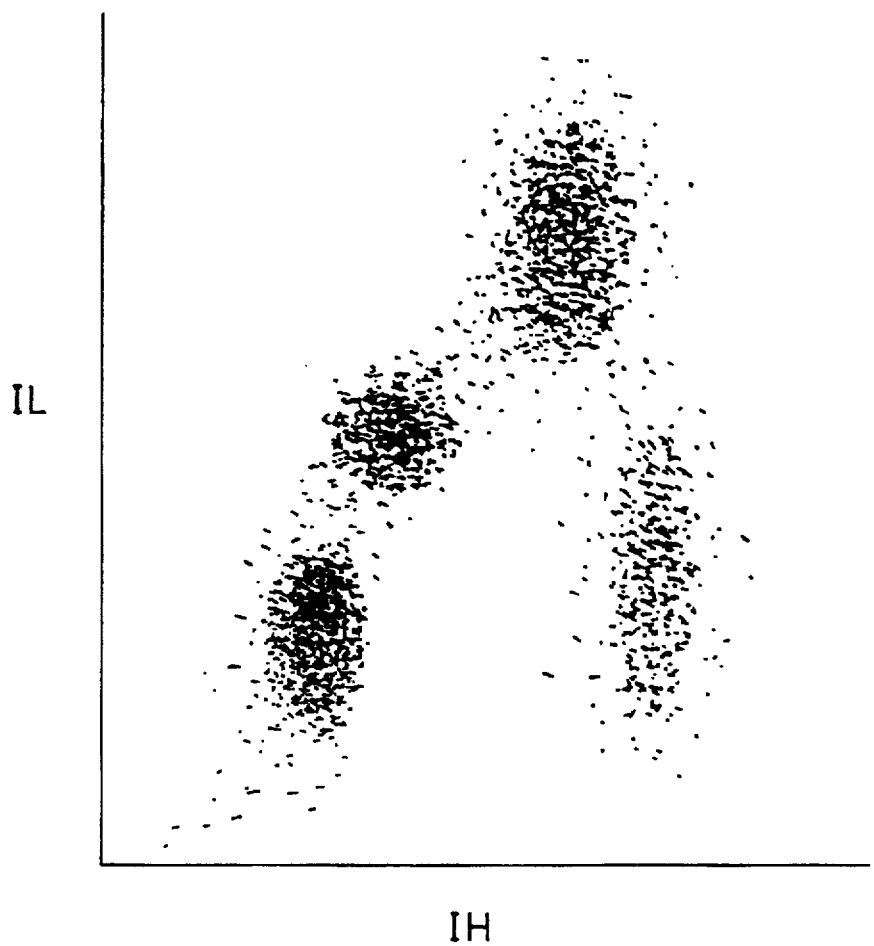
FIG. 5 is a view showing an example of scattergram prepared in the preferred example according to the present invention.

FIG. 5 shows an example of a distribution, namely a scattergram, displayed when leukocytes are classified in the apparatus 100 for analyzing particles.

Here, the lateral axis (X axis) represents the intensity IH of the high-angle forward scattered light pulse, whereas the vertical axis (Y axis) represents the intensity IL of the low-angle forward scattered light pulse.

Figure 6:
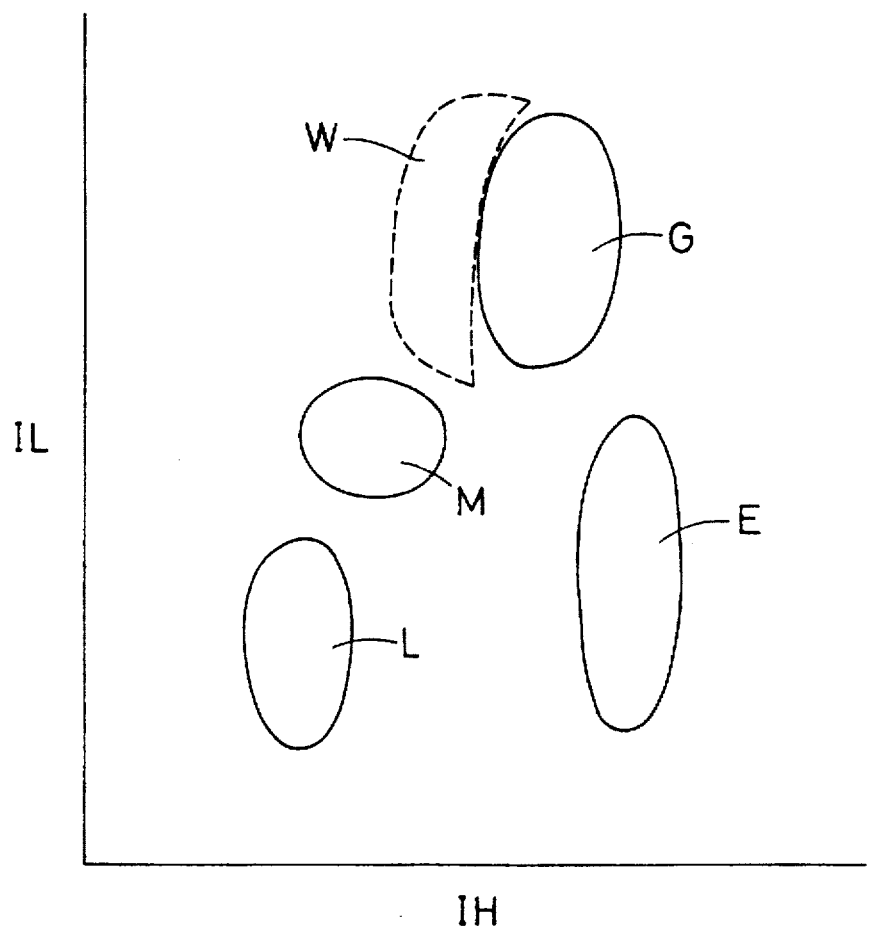
FIG. 6 is an explanatory view showing a group in FIG. 5.

In this scattergram, leukocytes are classified into four groups as shown in FIG. 6 with lymphocytes being classified as group (cluster) L, monocytes as group M, granulocytes other than eosinophils as group G, and eosinophils as group E.

Figure 7:
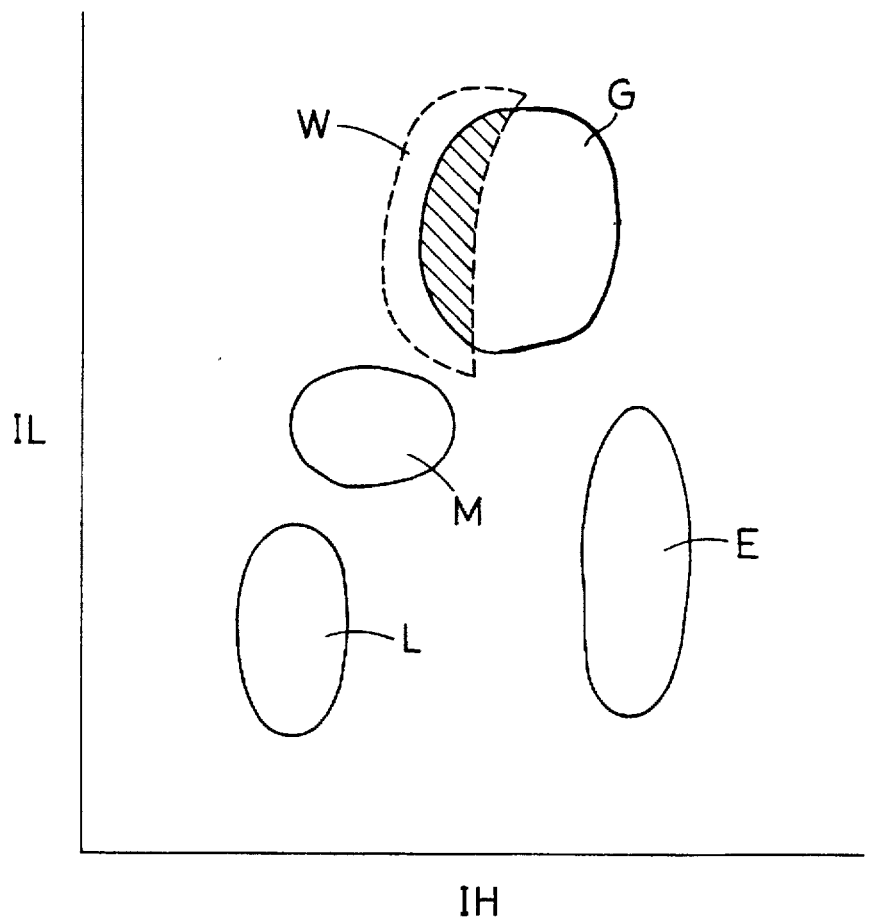
FIG. 7 is an explanatory view showing a judgement region of the preferred example according to the present invention.

Referring to FIG. 6, the region W surrounded by a broken line is an example of an abnormal-particle judgement region (hereafter referred to as "judgement region") which is set beforehand in the signal analyzer 7. (In this example, the region W is assumed to be a region where immature granulocytes appear). If the cells to be detected (immature granulocytes) appear (are plotted) in the region W as shown in FIG. 7, the signal analyzer 7 counts the number of appearing cells and, if the number exceeds a predetermined value, a message such as "POSITIVE" and a message corresponding to the appearance of the abnormal cells (immature granulocytes) are displayed in a display device 8.

Here, the judgement region may be set for blast cells, left shifts, heteromorphous lymphocytes, nucleated erythrocytes, or the like besides the above immature granulocytes, although the explanation thereof is omitted.

Accordingly, the apparatus 100 for analyzing particles makes it possible to efficiently conduct a screening test on a plurality of different specimens.

Next, a method and an apparatus for determining the judgement region will be hereafter explained.

Figure 8:
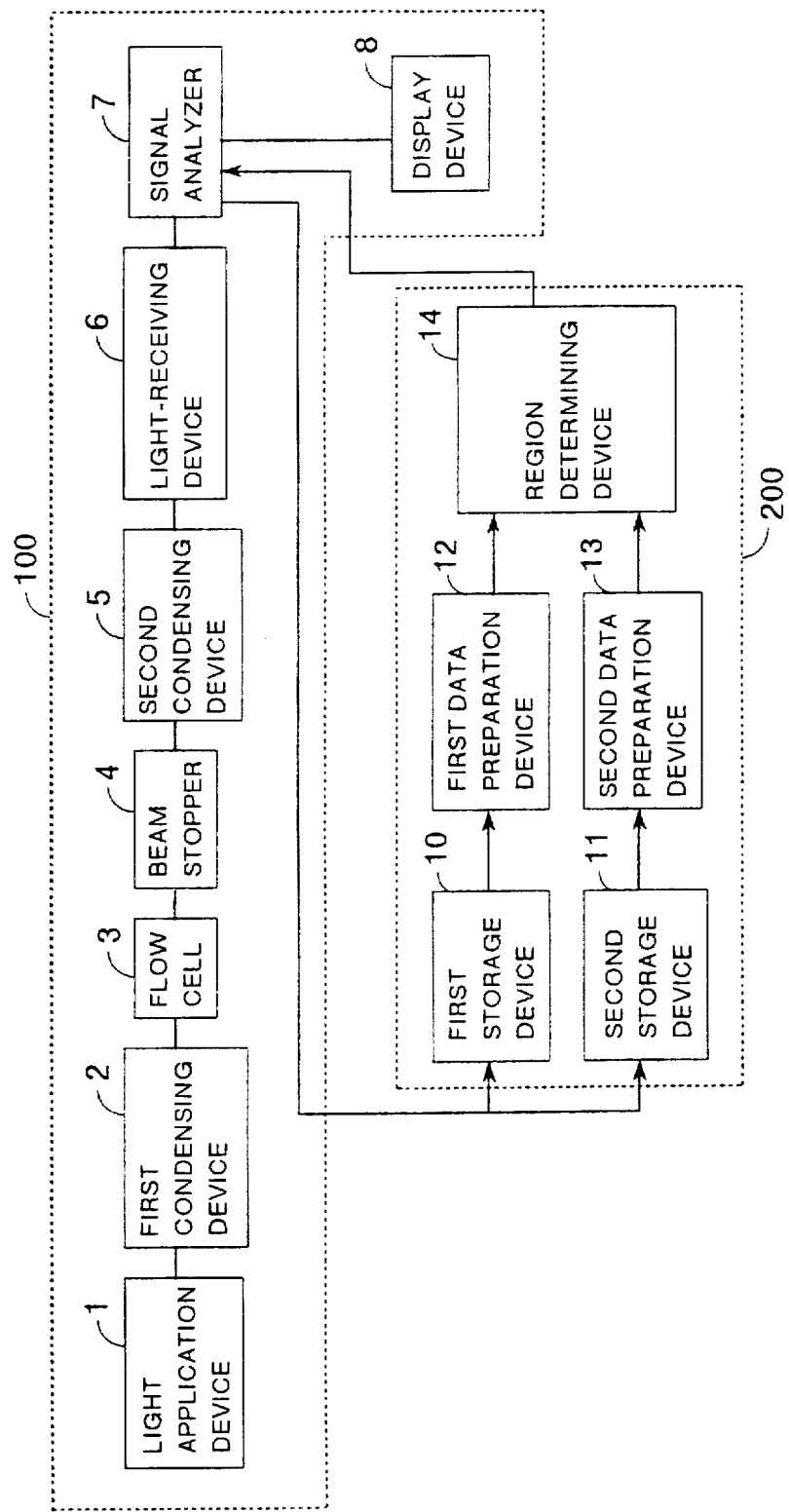
FIG. 8 is a block diagram showing an apparatus for determining a judgement region, the apparatus being applied to the preferred example of FIG. 1.

As shown in FIG. 8, an apparatus 200 for determining the particle judgement base is connected to the signal analyzer 7 in the apparatus 100 for analyzing particles. The apparatus 200 for determining the particle judgement base includes a first storage device 10, a second storage device 11, a first data preparation device 12, a second data preparation device 13, and a region determining device 14, and is constructed with a microcomputer or a personal computer.

A plurality of normal specimens and a plurality of abnormal specimens (here, specimens in which immature granulocytes appear) are analyzed in the apparatus 100 for analyzing particles to prepare a scattergram for each.

The apparatus 200 receives the data of each scattergram from the signal analyzer 7, determines the judgement region by employing the following two methods, namely, (1) particle frequency method and (2) particle probability method, and sets the determined region in the signal analyzer 7 as shown by the region W in FIG. 6. At this time, the after-mentioned base Point (region base point) for positioning the judgement region is also set in the signal analyzer 7.

(1) Particle frequency method

Figure 9:
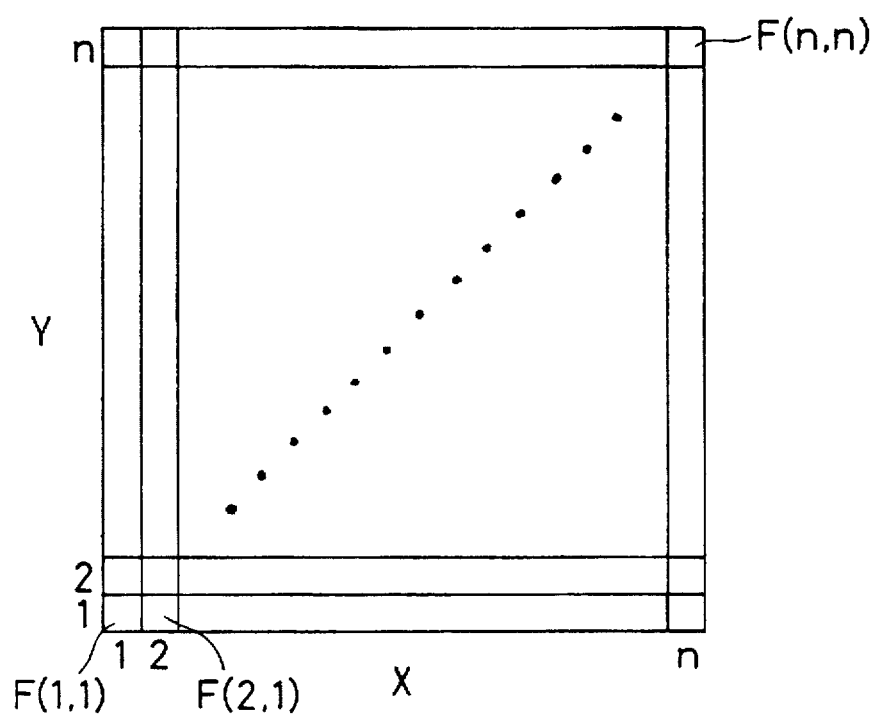
FIG. 9 is an explanatory view showing coordinates in a scattergram of the preferred example according to the present invention.

For simplicity of explanation, the coordinates (the address)(X,Y) of each dot on the plane of the scattergram shown in FIG. 5 are defined as in FIG. 9, and the frequency on each of the address is represented as F(X,Y). In other words, the distribution data representing the scattergram is represented as F(X,Y) (n=256, for example, in FIG. 9). For each of N cases (for example, 200 cases) of normal specimens, a scattergram is prepared in the apparatus 100 for analyzing particles. The N distribution data $F_1(X,Y)$, $F_2(X,Y)$, ..., and $F_N(X,Y)$ shown in FIG. 10(a) are stored in the first storage device 10 in the apparatus 200.

Next, for each of M cases (for example, 100 cases) of abnormal specimens (specimens in which immature granulocytes appear), a scattergram is prepared in the apparatus 100 for analyzing particles. The M distribution data $G_1(X,Y)$, $G_2(X,Y)$, ..., and $G_M(X,Y)$ shown in FIG. 10(b) are stored in the second storage device 11 in the apparatus 200. The first data preparation device 12 overlappingly stacks the distribution data stored in the first storage device 10 (the frequency is added address by address) as shown in FIG. 11(a).

Figure 12:
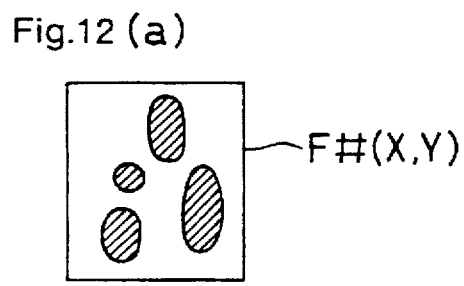
FIGS. 12(a) and 12(b) are explanatory views for showing a method of determining a judgement region in the preferred example according to the present invention.
Figure 12:
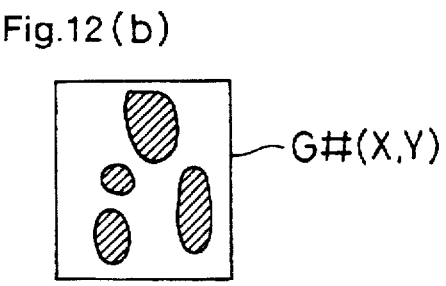

In other words, the distribution data F#(X,Y) of the basic normal scattergram is calculated from the following equation (1) as shown in FIG. 12(a).

$$F\#(X,Y)=F_1(X,Y)+F_2(X,Y)+\ldots+F_N(X,Y) \tag{1}$$

Figure 11:
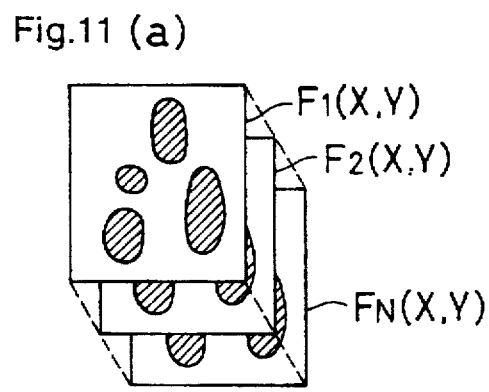
FIGS. 11(a) and 11(b) are explanatory views for showing a method of determining a judgement region in the preferred example according to the present invention.
Figure 11:
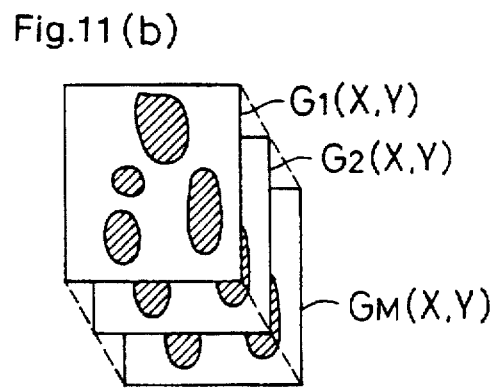

On the other hand, the second data preparation device 13 overlappingly stacks the distribution data stored in the second storage device 11 (the frequency is added address by address), as shown in FIG. 11(b).

In other words, the distribution data G#(X,Y) of the basic abnormal scattergram is calculated from the following equation (2) as shown in FIG. 12(b).

$$G\#(X,Y)=[G_1(X,Y)+G_2(X,Y)+\ldots+G_M(X,Y)]\cdot(N/M) \tag{2}$$

Here, the multiplier (N/M) on the right side of the equation (2) is for adjusting the number of data to be the same as in the equation (1).

Figure 13:
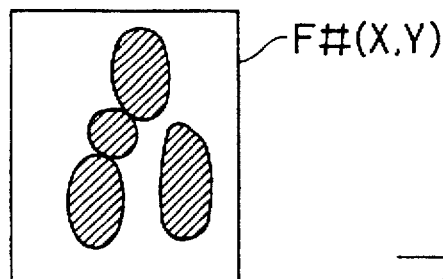
FIGS. 13(a) and 13(b) are explanatory views for showing a method of determining a judgement region in the preferred example according to the present invention.
Figure 13:
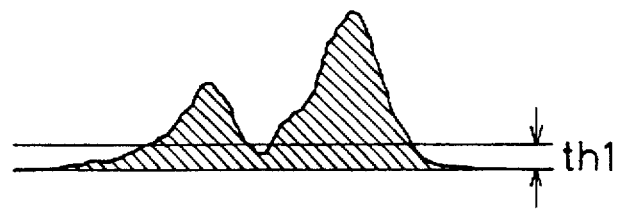
Figure 14:
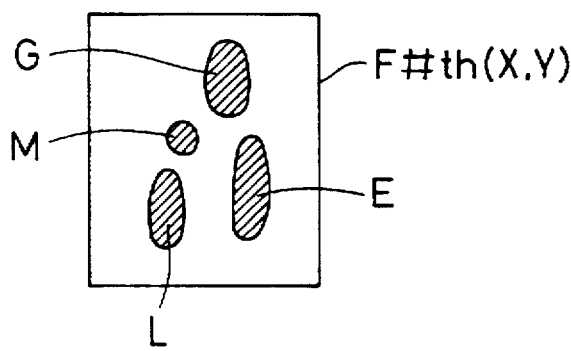
FIGS. 14(a) and 14(b) are explanatory views for showing a method of determining a judgement region in the preferred example according to the present invention.
Figure 14:
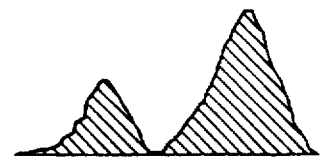

If the scattergram represented by the distribution data F#(X,Y) shown in FIG. 12(a) becomes like that of FIG. 13 (a) by including the unnecessary components such as noise, and its cross-sectional histogram has a broadened foot such as shown in FIG. 13(b), the foot is cut off at a predetermined threshold value th1, the scattergram and the histogram being modified as shown in FIGS. 14(a) and (b).

In other words, $F\#_{th}(X,Y)$ which is shown in FIG. 14(a) and calculated by the following equation (3) becomes the distribution data of the fundamental normal scattergram.

$$F\#_{th}(X,Y)=F\#(X,Y)-th1(F\#(X,Y)>th1) \tag{3}$$

$$F\#_{th}(X,Y)=0(F\#(X,Y)\leq th1)$$

The region determining device 14 determines the judgement region as follows.

Figure 15:
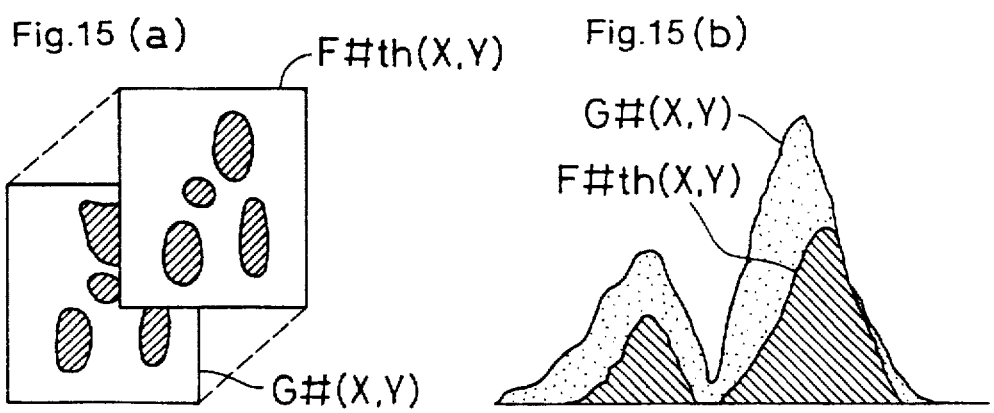
FIGS. 15(a) and 15(b) are explanatory views for showing a method of determining a judgement region in the preferred example according to the present invention.

First, the fundamental normal scattergram $F\#_{th}(X,Y)$ is cut out from the fundamental abnormal scattergram $G\#_{th}(X,Y)$ as shown in FIGS. 15(a) and (b).

Figure 16:
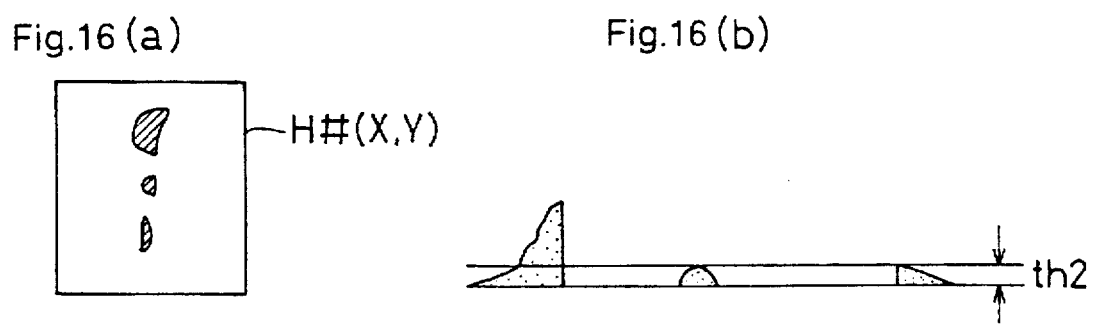
FIGS. 16(a) and 16(b) are explanatory views for showing a method of determining a judgement region n the preferred example according to the present invention.

As a result of this, a scattergram H#(X,Y) such as shown in FIG. 16(a) is obtained. FIG. 16(b) shows its cross-sectional histogram. In other words, H#(X,Y) is calculated as follows.

$$H\#(X,Y)=G\#(X,Y) \text{ (if } F\#_{th}(X,Y)=0) \tag{4}$$

$$H\#(X,Y)=0 \text{(if } F\#_{th}(X,Y)>0)$$

Here as shown in FIG. 16(a) a plurality of regions may have been obtained. Accordingly, in order to have only one region, the foot of the histogram is cut off at a threshold value th2, as shown in FIG. 16(b). In other words, the following operation is carried out.

$$H\#_{th}(X,Y)=H\#(X,Y)-th2(H\#(X,Y)>th2) \tag{5}$$

$$H\#_{th}(X,Y)=0(H\#(X,Y) \leq th2)$$

Figure 17:
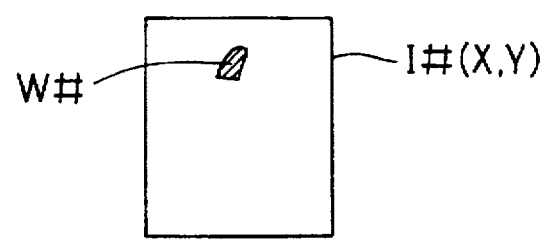
FIG. 17 is an explanatory view for showing a method of determining a judgement region in the preferred example according to the present invention.

Next, the following operation is carried out to determine a distribution data I#(X,Y) representing the judgement region W# shown in FIG. 17.

$$I\#(X,Y)=1(H\#_{th}(X,Y)>0) \tag{6}$$

$$I\#(X,Y)=0(H\#_{th}(X,Y)=0)$$

(2) Particle probability method

Figure 10:
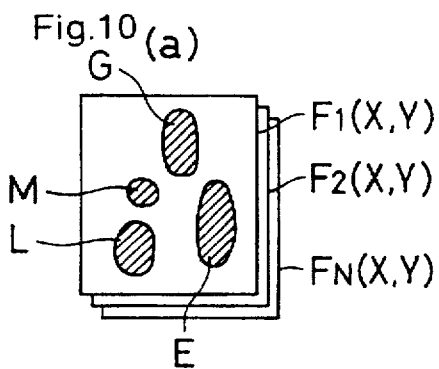
FIGS. 10(a) and 10(b) are explanatory views for showing a method of determining a judgement region in the preferred example according to the present invention.
Figure 10:
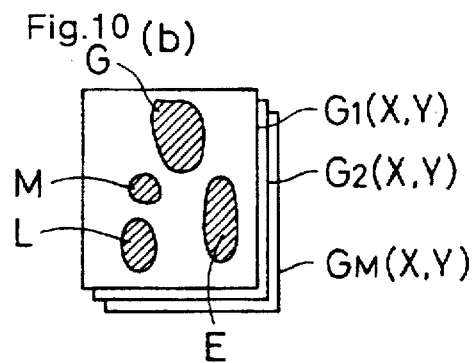

As shown above, when the distribution data of the scattergrams prepared from the normal specimens and the abnormal specimens are stored in the first storage device 10 and the second storage device 12, respectively, as shown in FIGS. 10 (a) and (b), the first data preparation device 12 and the second data preparation device 13 normalize the distribution data of each of the scattergrams using the following equation.

$$F_k\%(X,Y) = \frac{F_k(X,Y)}{\sum_{X=1}^{n}\sum_{Y=1}^{n} F_k(X,Y)} \quad (k=1,2,\ldots,N) \tag{7}$$

$$G_k\%(X,Y) = \frac{G_k(X,Y)}{\sum_{X=1}^{n}\sum_{Y=1}^{n} G_k(X,Y)} \quad (k=1,2,\ldots,M) \tag{8}$$

Here, to normalize is to calculate the ratio (%) of the number of cells (i.e. probability of appearance) at each dot in the scattergram relative to the total number of cells in the scattergram and to modify the scattergram based on the ratio.

Figure 18A:
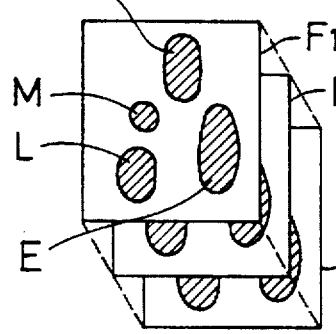
FIGS. 18(a) and 18(b) are explanatory views for showing a method of determining a judgement region in the preferred example according to the present invention.
Figure 18B:
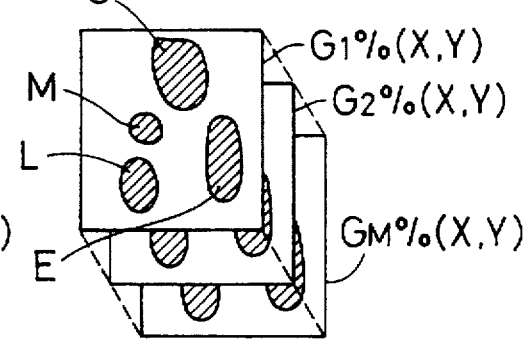

Then, the first data preparation device 12 and the second data preparation device 13 overlappingly stack each of the distribution data (the frequency is added address by address), as shown in FIGS. 18(a) and (b).

Figure 19A:
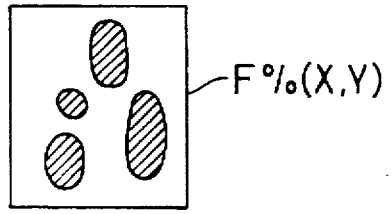
FIGS. 19(a) and 19(b) are explanatory views for showing a method of determining a judgement region in the preferred example according to the present invention.
Figure 19B:
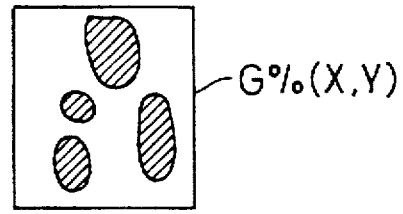

In other words, the distribution data F%(X,Y) of the fundamental normal scattergram and the distribution data G%(X,Y) of the fundamental abnormal scattergram are calculated from the following equations (9) and (10), respectively, as shown in FIGS. 19(a) and (b).

$$F\%(X,Y)=F_1\%(X,Y)+F_2\%(X,Y)+\ldots+F_N\%(X,Y) \tag{9}$$

$$G\%(X,Y)=[G_1\%(X,Y)+G_2\%(X,Y)+\ldots+G_M\%(X,Y)]\cdot(N/H) \tag{10}$$

The region determining device 14 then determines the judgement region as follows. First, the distribution data G%(X,Y) of the fundamental abnormal scattergram is divided by the distribution data F%(X,Y) of the fundamental normal scattergram to give H%(X,Y) as shown in the following equation.

$$H\%(X,Y)=G\%(X,Y) / F\%(X,Y) \; (G\%(X,Y) \leq F\%(X,Y)) \tag{11}$$

$$H\%(X,Y)=0(G\%(X,Y)<F\%(X,Y))$$

Figure 20:
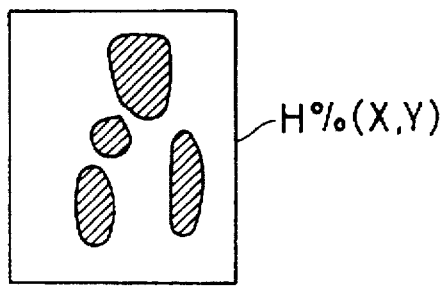
FIGS. 20(a) and 20(b) are explanatory views for showing a method of determining a judgement region in the preferred example according to the present invention.
Figure 20:
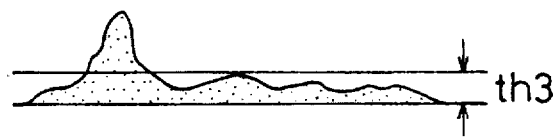

Based on the scattergram shown by H%(X,Y) in FIG. 20(a), the foot of the histogram is cut off at a threshold value th3, as shown in FIG. 20(b). In other words, the following operation is conducted. FIG. 20(b) is a cross-sectional histogram of an essential part of FIG. 20(a).

$$H\%_{th}(X,Y)=H\%(X,Y)-th3 \; (H\%(X,Y)>th3) \tag{12}$$

$$H\%_{th}(X,Y)=0(H\%(X,Y) \leq th3)$$

Figure 21:
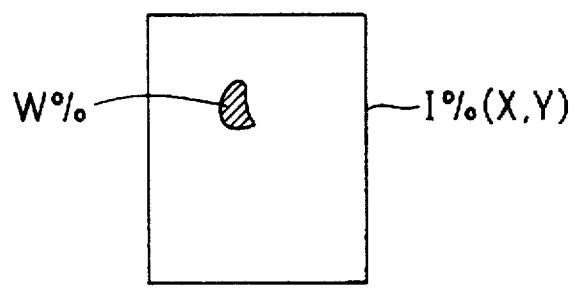
FIG. 21 is an explanatory view for showing a method of determining a judgement region in the preferred example according to the present invention.

Next, the following operation is carried out to determine a distribution data I%(X,Y) representing the judgement region W% shown in FIG. 21.

$$I\%(X,Y)=1(H\%_{th}(X,Y)>0) \tag{13}$$

$$I\%(X,Y)=0(H\%_{th}(X,Y)=0)$$

Figure 22:
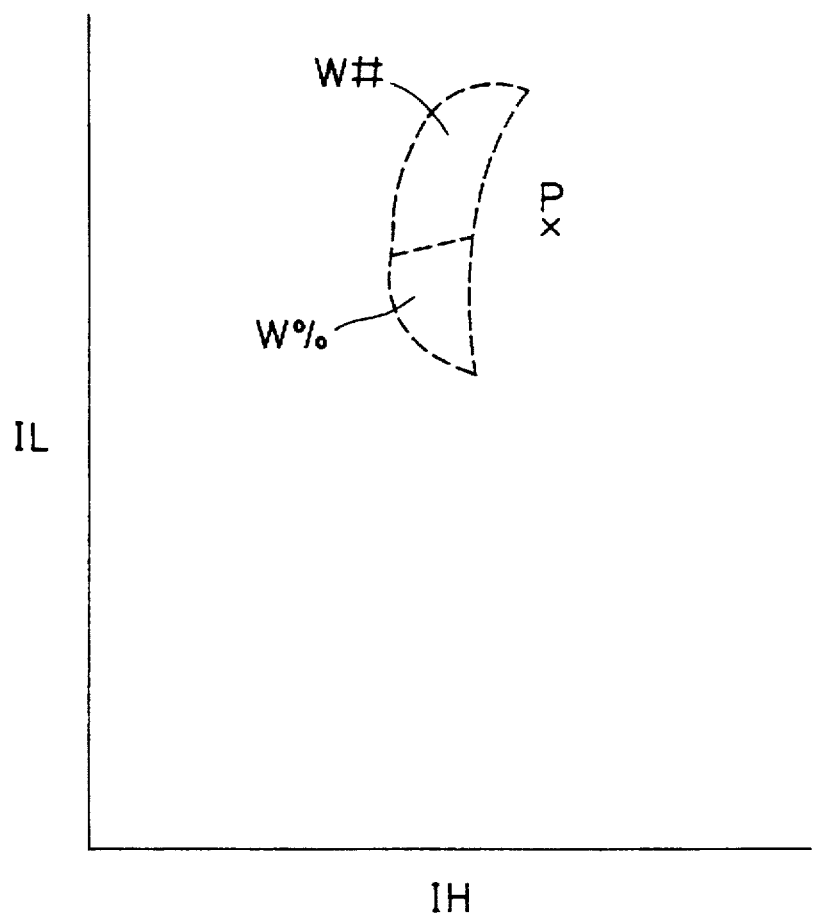
FIG. 22 is an explanatory view showing a base point of a judgement region in a scattergram of the preferred example according to the present invention.

When the region data of the judgement regions W# and W% are thus calculated, the region determining device 14 calculates the coordinates of the base point P (hereafter referred to as "region base point"), namely P($m_1$, $n_1$), for positioning these regions as a statistical center of gravity of the group G in the scattergram obtained from the equation (1) or (3). These region data and the coordinates of the region base point are set in the signal analyzer 7 as shown in FIG. 22.

The method and the apparatus for correcting the judgement region set as above will be hereinafter explained.

Figure 25:
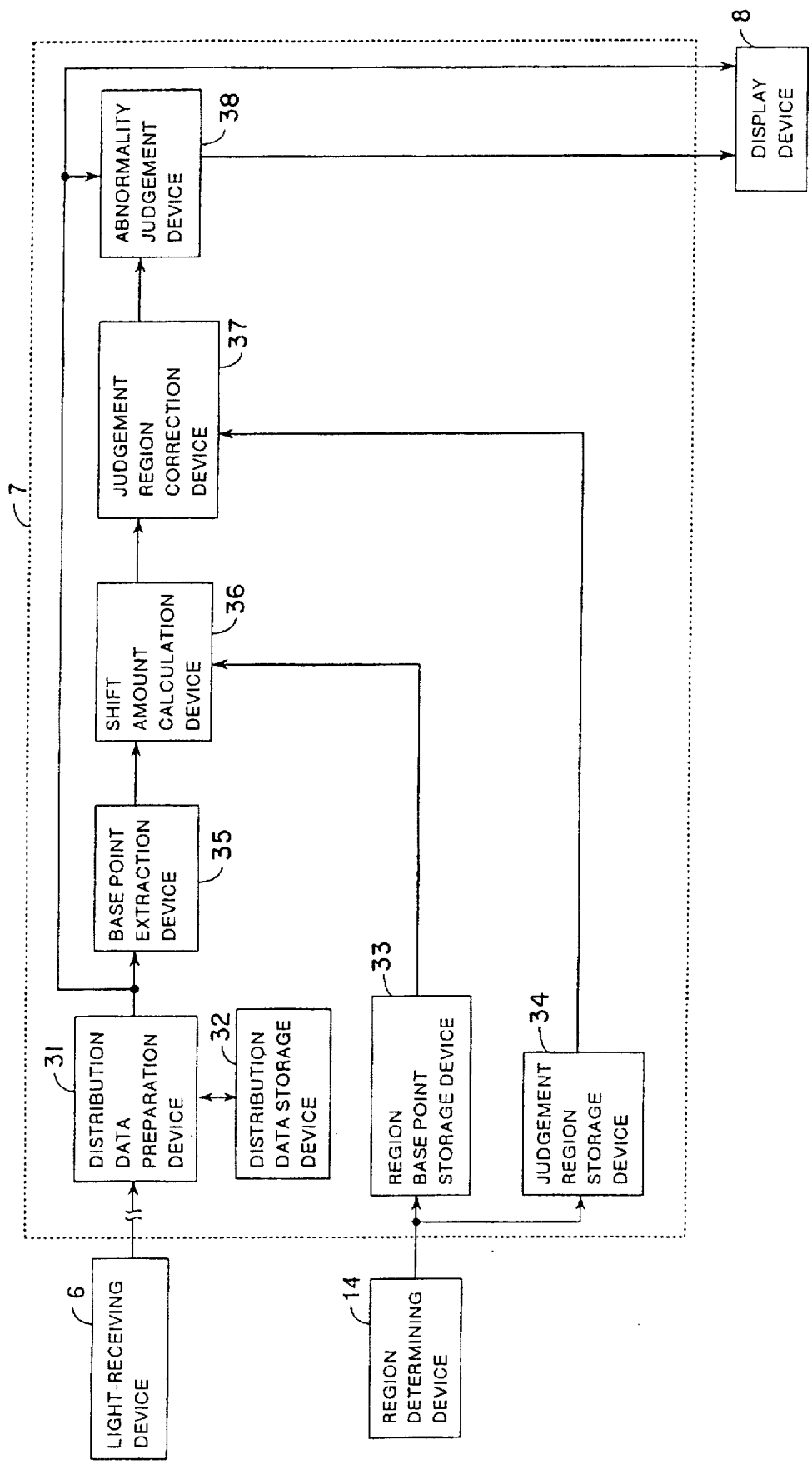
FIG. 25 is a block diagram showing, in detail, an essential part of FIG. 1.

FIG. 25 is a detailed block diagram of the signal analyzer 7 shown in FIG. 1. The signal analyzer 7 includes a distribution data preparation device 31 for preparing a distribution data (distribution figure) of a scattergram upon receiving the signal from the light receiving device 6, a distribution data storage device 32 for storing the prepared distribution data, a base point extraction device 35 for extracting a group base point indicating the position of each group in the distribution data of the scattergram, a region base point storage device 33 for storing the region base point calculated by the region determining device 14, a judgement region storage device 34 for storing the judgement region determined by the region determining device 14, a shift amount calculation device 26 for calculating the shift amount of the judgement region by comparing the coordinates of the group base point and the region base point, a judgement region correction device 37 for correcting the position of the judgement region on the scattergram based on the shift amount, and an abnormality judgement device 38 for conducting a judgement on abnormality by counting the number of cells appearing in the judgement region.

Figure 23:
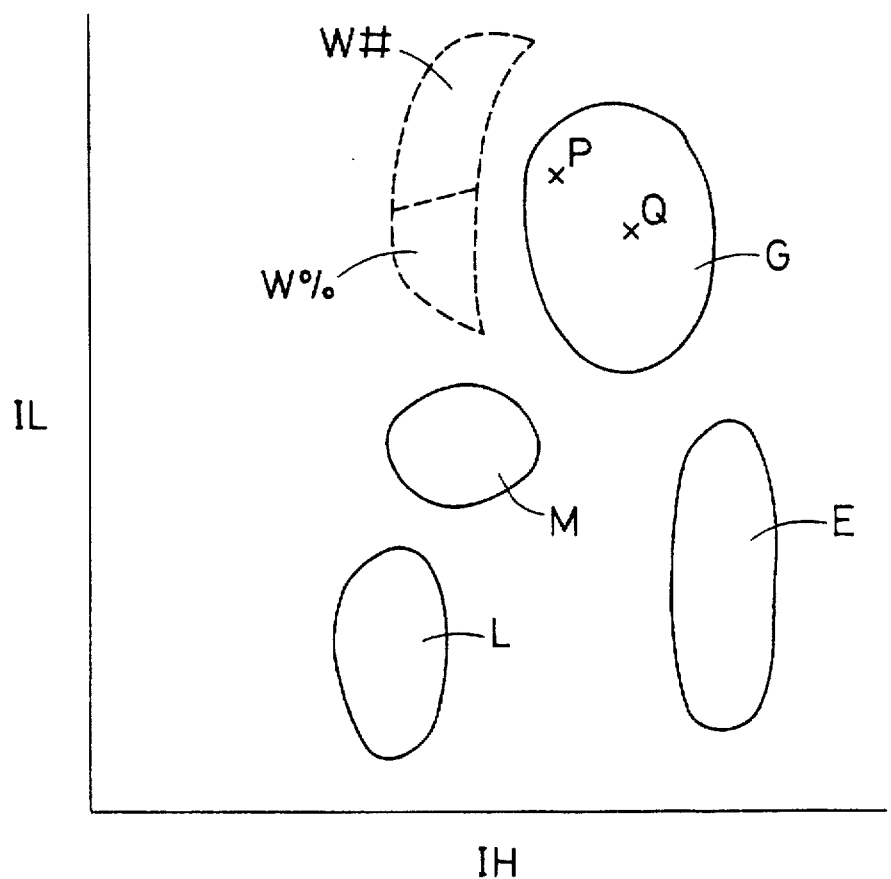
FIG. 23 is an explanatory view showing a position relationship between a judgement region and a group in a scattergram of the preferred example according to the present invention.

When one specimen to be examined is supplied to the flow cell 3, the distribution data preparation device 31 of the signal analyzer 7 prepares a scattergram based on the specimen, as shown in FIG. 23, and stores the distribution data in the distribution data storage device 32. Then, the base point extraction device 25 calculates a statistical center of gravity Q($m_2$, $n_2$) of the group G in the prepared scattergram and extracts it as the group base point.

The shift amount calculation device 36 calculates the shift amount $\Delta X=m_2-m_1$, $\Delta Y=n_2-n_1$ which is necessary for making the region base point P($m_1$, $n_1$) of the judgement regions W# and W% identical to the group base point Q($m_2$, $n_2$).

Figure 24:
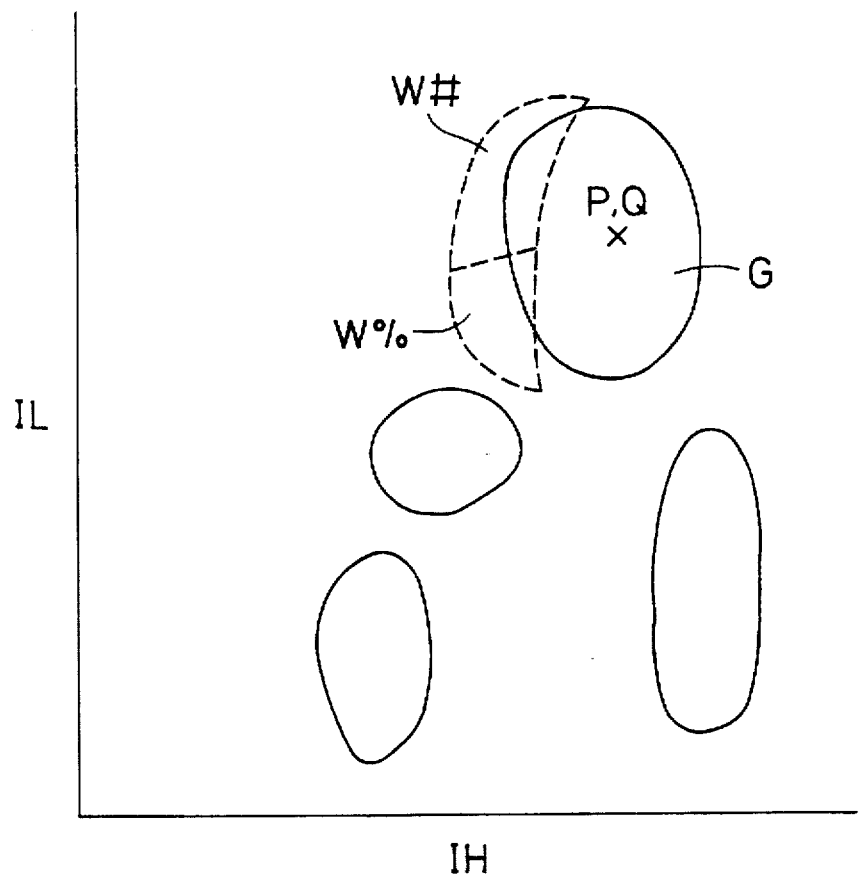
FIG. 24 is an explanatory view showing a method for correcting the position of a judgement region in a scattergram of the preferred example according to the present invention.

The judgement region correction device 37 corrects the position of the judgement regions W# and W%, as shown in FIG. 24 by transferring the judgement regions by the calculated shift amount. The abnormality judgement device 38 counts the number of cells appearing within the corrected judgement region in the scattergram and makes the display device 8 display the message corresponding to the counted number of cells.

According to the present invention, even if the position of a group shown on a scattergram varies, the position of the judgement region is corrected in accordance with the variation, so that the dispersion in the measurement characteristics among the apparatuses for analyzing particles and the dispersion among the specimens are absorbed, thus contributing to the improvement of the judgement precision in examining the specimens.

What we claim is:

1. An apparatus for analyzing particles comprising:

distribution data preparation means for measuring parameters that characterize particles contained in a specimen and for preparing distribution data of the particles in a coordinate space based on the parameters;

judgement region storage means for storing in advance a predetermined judgement region in the coordinate space;

base point extraction means for extracting, when the distribution data forms at least one group, a group base point that shows a position of the group;

judgement region correction means for shifting a position of the judgement region in the coordinate space by referring to each group base point extracted every time a distribution data is prepared by the distribution data preparation means; and judgement means for judging abnormality of the specimen based on the particles present within the shifted judgement region.

2. The apparatus according to claim 1, in which the judgement region storage means stores in advance the judgement region and a region base point representing a position of the judgement region with respect to the group base point, and in which the correction means corrects the position of the judgement region so that a relative position of the group base point and the region base point is maintained to be constant.

3. The apparatus according to claim 1, in which the group base point is a center of gravity of the group.

4. The apparatus according to claim 3, in which, when the distribution data forms a plurality of groups, the base point extraction means extracts the group base point on the basis of centers of gravity of at least two groups.

5. The apparatus according to claim 1, in which the parameter comprises two parameters obtained from an optical measurement of the particles, and in which the distribution data comprises a scattergram formed by plotting a frequency of particles on a two-dimensional coordinate plane with respect to the two parameters.

6. The apparatus according to claim 1, in which the specimen is a blood sample.

7. The apparatus according to claim 6, in which the predetermined judgement region is a region where abnormal particles comprising at least one kind of cells selected from blast cells, immature granulocytes, left shift cells, and nucleated mature granulocytes are expected to appear.

8. The apparatus according to claim 6, in which the group is a cell group selected from monocytes, lymphocytes, eosinophils, and granulocytes other than eosinophils.

9. The apparatus according to claim 2, in which the judgement region and the region base point are supplied to the judgement region storage means by a determining device which determines the judgement region and The region base point.

10. The apparatus according to claim 9, in which the determining device includes:

first storage means for storing each distribution data of a first specimen group which belongs to a first category;

second storage means for storing each distribution data of a second specimen group which belongs to a second category;

first data preparation means for preparing a first fundamental distribution data by accumulating each distribution data of the first specimen group;

second data preparation means for preparing second fundamental distribution data by accumulating each distribution data of the second specimen group; and region determining means for determining, as the judgement region, a region on the distribution data where peculiar particles exist in the first or second category by comparing the first fundamental distribution data with the second fundamental distribution data and for determining the region base point based on an arrangement relation between the judgement region and the first or second fundamental distribution data.

11. The apparatus according to claim 10, wherein the first specimen group which belongs to the first category is a normal specimen group comprising normal particles, the second specimen group which belongs to the second category is an abnormal specimen group comprising normal and abnormal particles, and the peculiar particles are the abnormal particles.

12. The apparatus according to claim 10, wherein the distribution data of the particles comprises an address and frequency of each particle in a distribution chart, and the first and second data preparation means prepare the first and second fundamental distribution data by adding the frequency of each distribution data for each address.

13. The apparatus according to claim 10, wherein the region determining means calculates, as the judgement region, a region on the distribution data where only one of the first and second fundamental distribution data exists by comparing the first fundamental distribution data with the second fundamental distribution data.

14. The apparatus according to claim 10, wherein the region determining means calculates a ratio of the first fundamental distribution data to the second fundamental distribution data and determines, as the judgement region, a region on the distribution data where the ratio is greater than a predetermined value.

15. The apparatus according to claim 1, wherein said judgement means further includes output means for outputting a signal indicating whether the specimen is abnormal when the particles present in the corrected judgement region exceed a predetermined amount.

16. The apparatus according to claim 15, further comprising a display for displaying said signal.

17. A method for analyzing particles comprising the steps of:

measuring parameters that characterize particles contained in a specimen;

preparing a distribution data of the particles in a coordinate space based on the parameters;

storing a predetermined judgement region in the coordinate space;

extracting, when the distribution data forms at least one group, a group base point that shows a position of the group;

shifting a position of the judgement region in the coordinate space by referring to each group base point extracted every time a distribution data is prepared by the distribution data preparation means; and judging abnormality of the specimen based on the particles present within the shifted judgement region.

18. The method according to claim 17, wherein said storing includes storing a region base point representing a position of the judgement region with respect to the group base point, and said shifting includes adjusting a position of the judgement region so that a relative position of the group base point and the region base point remains constant.

19. The method according to claim 17, further comprising outputting a signal indicating whether the specimen is abnormal when the particles present in a corrected judgement region exceed a predetermined amount.

20. The method according to claim 19, further comprising displaying said signal.

* * * * *